(12) United States Patent
Cannell et al.

(10) Patent No.: US 7,981,403 B2
(45) Date of Patent: Jul. 19, 2011

(54) ARTIFICIAL HAIR COLOR REMOVAL COMPOSITIONS AND METHODS

(75) Inventors: David W. Cannell, Plainfield, NJ (US); Karen M. Saiewitz, Kenilworth, NJ (US); Michael S. DeGeorge, Middletown, NJ (US)

(73) Assignee: L'Oreal, Paris (FR)

( * ) Notice: Subject to any disclaimer, the term of this patent is extended or adjusted under 35 U.S.C. 154(b) by 1258 days.

(21) Appl. No.: 11/543,783

(22) Filed: Oct. 6, 2006

(65) Prior Publication Data

US 2008/0085249 A1   Apr. 10, 2008

(51) Int. Cl.
*A61K 8/00* (2006.01)
*A61K 8/18* (2006.01)
*A61Q 5/08* (2006.01)

(52) U.S. Cl. .......................................... 424/62; 424/70.1

(58) Field of Classification Search .................. None
See application file for complete search history.

(56) References Cited

U.S. PATENT DOCUMENTS

| 3,892,845 | A | * | 7/1975 | Cunningham et al. .......... 424/62 |
| 5,474,578 | A | * | 12/1995 | Chan et al. ........................ 8/431 |
| 5,785,961 | A | | 7/1998 | Nakama et al. |
| 6,171,347 | B1 | | 1/2001 | Kunz et al. |
| 6,669,739 | B2 | | 12/2003 | Sauter et al. |
| 2006/0162096 | A1 | | 7/2006 | Pasquier et al. |

FOREIGN PATENT DOCUMENTS

| EP | 1 598 050 | 11/2005 |
| EP | 1 598 051 | 11/2005 |
| JP | 2002-226343 | 8/2002 |
| JP | 2002-226344 | 8/2002 |
| JP | 2004-107290 | 8/2004 |
| WO | WO 2004/078152 | 9/2004 |

* cited by examiner

*Primary Examiner* — Anand Desai
*Assistant Examiner* — Melissa S Mercier
(74) *Attorney, Agent, or Firm* — Oblon, Spivak, McClelland, Maier & Neustadt, L.L.P.

(57) ABSTRACT

The invention relates to methods for removing artificial color from hair comprising combining a first composition comprising a sulfur reducing agent with a second composition comprising an oxidizing agent to form a color removing composition, and using the color removing composition to remove artificial color from the hair, as well as to compositions and kits containing such compositions which are useful in such methods.

21 Claims, No Drawings

ARTIFICIAL HAIR COLOR REMOVAL COMPOSITIONS AND METHODS

FIELD OF THE INVENTION

The present invention generally relates to methods for removing artificial color from hair comprising combining a first composition comprising a sulfur reducing agent with a second composition comprising an oxidizing agent to form a color removing composition, and using the color removing composition to remove artificial color from the hair, as well as to compositions and kits containing such compositions which are useful in such methods.

BACKGROUND OF THE INVENTION

Artificial colorants for hair (for example, hair dyes) and methods for artificially coloring hair are well-known. Generally speaking, artificial colorants for hair function either by depositing colorants on the hair's exterior and/or by depositing colorants within the hair shaft. Removing such colorants from the exterior or interior of hair typically involves interfering with the hair/colorant interaction sufficiently to cause the colorant to dislodge from the hair.

U.S. Pat. No. 5,785,961 discloses mixing at the time of use-type methods and compositions for dyeing or bleaching hair. Specifically, the '961 patent discloses combining a first composition containing either a dye or a bleaching agent such as ammonia, an anionic surfactant and a higher fatty acid with a second composition containing an oxidizing agent such as hydrogen peroxide before use to form a composition to dye or bleach hair. However, the '961 patent does not disclose how to remove artificial colorants from hair. The '961 patent's dye compositions clearly do not remove artificial color from hair—instead, they provide artificial color to hair. The '961 patent's bleaching compositions also do not remove artificial color from hair. Rather, the bleaching agents in such compositions oxidize the melanin in hair by removing sulfur from it, thereby removing the natural hair color in an irreversible chemical reaction (oxidized melanin is substantially colorless).

Accordingly, the present invention addresses the need in the art for methods and compositions for removing artificial color from hair.

SUMMARY OF THE INVENTION

The present invention relates to methods for removing artificial color from hair comprising combining a first composition comprising a sulfur reducing agent with a second composition comprising an oxidizing agent to form a color removing composition, and using the color removing composition to remove artificial color from the hair.

The present invention also relates to methods for highlighting hair by lightening the artificial color of hair comprising combining a first composition comprising a sulfur reducing agent with a second composition comprising an oxidizing agent to form a color removing composition, and using the color removing composition to remove artificial color from portion(s) of the hair to highlight the hair. These methods can further comprise artificially coloring hair prior to removing artificial color from portion(s) of the hair to highlight the hair.

The present invention also relates to two compositions useful for removing artificial color from hair. The first composition comprises a sulfur reducing agent. The second composition comprises an oxidizing agent.

The present invention also relates to kits useful for removing artificial color from hair. The kits comprise a first composition comprising a sulfur reducing agent, a second composition comprising an oxidizing agent, and instructions for combining the first composition and the second composition to form a color removing composition and for using the color removing composition to remove artificial color from the hair.

It is to be understood that both the foregoing general description and the following detailed description are exemplary and explanatory only, and are not restrictive of the invention.

DETAILED DESCRIPTION OF THE INVENTION

Other than in the operating examples, or where otherwise indicated, all numbers expressing quantities of ingredients and/or reaction conditions are to be understood as being modified in all instances by the term "about".

As used herein, the expression "at least one" means one or more and thus includes individual components as well as mixtures/combinations.

"Cosmetically acceptable medium" means a medium that is compatible with any keratin material, such as the skin, the hair, the nails, the eyelashes, the eyebrows, the lips and any other area of body or facial skin.

The cosmetic compositions and methods of the present invention can comprise, consist of, or consist essentially of the essential elements and limitations of the invention described herein, as well as any additional or optional ingredients, components, or limitations described herein or any otherwise useful ingredient found in personal care compositions intended for application to keratin materials.

The compositions of the present invention may be in any form. For example, they may be a liquid, a paste, a solid or a cream. The composition of the invention may be transparent or clear, including for example, a composition without pigments. The compositions of the present invention may also be in the form of a hair gel, a hair mousse, or a hair spray (aerosol or non-aerosol).

The compositions of the present invention can be in the form of an emulsion. Suitable emulsion forms include but are not limited to oil-in-water, water-in-oil, oil-in-water-in-oil, water-in-oil-in-water and nanoemulsions (emulsions whose oil globules are of very fine particle size, that is to say that they have a number-average size of less than about 100 nanometers (nm)). Emulsions contain at least one oil phase and at least one aqueous phase. Typically speaking, emulsions contain surfactants or surfactant-like materials which provide stability to the emulsions and inhibit de-phasing of the emulsions.

First Composition

According to the present invention, a first composition comprising at least one sulfur reducing agent is provided. By "reducing agent," it is meant that the agent causes another compound to be reduced (that is, lose oxygen). By "sulfur reducing agent," it is meant that the reducing agent contains sulfur.

In accordance with the present invention, any sulfur reducing agent can be used as long as it has sufficient reducing activity and contains sulfur. Acceptable reducing agents include, but are not limited to, sulfur hydroxyacids, salts of sulfur hydroxyacids, salts of sulfites or bisulfites, sulfur antioxidants, and mixtures thereof.

Acceptable sulfur hydroxyacids include sulfur containing derivatives of hydroxyacids. Preferred sulfur hydroxyacids include, but are not limited to, thioglycolic acid, thiolactic acid, thiocitric acid, thiomalic acid, thiosalicylic acid, and mixtures thereof. Particularly preferred sulfur alpha hydroxyacids are thioglycolic acid and thiolactic acid.

Acceptable salts of sulfur hydroxyacids include compounds containing a cation and an anion corresponding to a sulfur containing derivative of an hydroxyacid. Preferred anions corresponding to a sulfur hydroxyacid include, but are not limited to, the anions corresponding to thioglycolic acid, thiolactic acid, thiocitric acid, thiosalicylic acid and thiomalic acid. Preferred cations include, but are not limited to, alkali metals (sodium, potassium, etc.), alkaline earth metal (calcium, magnesium, etc.) and ammonium. Particularly preferred salts of sulfur alpha hydroxyacids include sodium thioglycolic acid (sodium thioglycolate), potassium thioglycolic acid (potassium thioglycolate), sodium thiolactic acid (sodium thiolactate), potassium thiolactic acid (potassium thiolactate), ammonium thiolactic acid (ammonium thiolactate), ammonium thioglycolic acid (ammonium thioglycolate), ethanolamine thioglycolic acid (ethanolamine thioglycolate), ethanolamine thiolactic acid (ethanolamine thiolactate), isooctyl thioglycolic acid (isooctyl thioglycolate), isooctyl thiolactic acid (isooctyl thiolactate), magnesium thioglycolic acid (magnesium thioglycolate), magnesium thiolactic acid (magnesium thiolactate), strontium thioglycolic acid (strontium thioglycolate), strontium thiolactic acid (strontium thiolactate), and mixtures thereof.

Acceptable salts of sulfites or bisulfites include compounds containing a cation and a bisulfite, metabisulfite, hydrosulfite, hydroxyalkane sulfite or sulfite anion. Preferred cations include, but are not limited to, alkali metals (sodium, potassium, etc.), alkaline earth metal (calcium, magnesium, etc.) and ammonium. Particularly preferred salts of sulfites or bisulfites include sodium sulfite, sodium bisulfite, potassium bisulfite, calcium bisulfite, magnesium bisulfite, ammonium bisulfite, ammonium sulfite, potassium metabisulfite, potassium sulfite, sodium hydrosulfite, sodium hydroxymethane sulfite, and mixtures thereof.

Other acceptable sulfur reducing agents include, but are not limited to, amino acids or amino acid derivatives containing sulfur such as, for example, cysteine, N-acetyl cysteine, and cysteamine HCL, dithiothreitol, glutathione, glyceryl thiopropionate zinc formaldehyde sulfoxylate and mercaptopropionic acid.

Preferably, the sulfur reducing agent is present in an amount ranging from about 1% to about 90% by weight of the total weight of the first composition, more preferably from about 2% to about 80% of the total weight of the first composition, more preferably from about 3% to about 70% of the total weight of the first composition, more preferably from about 4% to about 60% of the total weight of the first composition, and most preferably from about 20% to about 50% of the total weight of the first composition, including all ranges and subranges therebetween.

According to preferred embodiments, the first composition further comprises at least one alkalinizing agent. By "alkalinizing agent," it is meant that the agent raises the pH of the composition to which it is added. Acceptable alkalinizing agents include, but are not limited to, alkali metal carbonates and alkanolamines such as mono-, di- or tri-ethanolamine.

Preferably, the alkalinizing agent is present in an amount ranging from about 0.1% to about 20% by weight of the total weight of the first composition, more preferably from about 0.5% to about 15% of the total weight of the first composition, more preferably from about 1% to about 10% of the total weight of the first composition, and most preferably from about 2% to about 6% of the total weight of the first composition, including all ranges and subranges therebetween.

According to preferred embodiments of the present invention, the first composition is substantially free of oxidizing agents (i.e., contains less than about 1% of oxidizing agent). In another embodiment, the first composition is essentially free of oxidizing agent (i.e., contains less than about 0.3% of oxidizing agent). In another embodiment, the first composition is free of oxidizing agents (i.e., contains less than about 0.1% of oxidizing agent). In yet another embodiment, the first composition contains no oxidizing agent.

According to preferred embodiments of the present invention, the first composition is substantially free of higher fatty acids of the general formula RCOOH, where R is a saturated or unsaturated hydrocarbon having on average 7-25 carbon atoms (i.e., contains less than about 0.1% of higher fatty acids). In another embodiment, the first composition is essentially free of higher fatty acids (i.e., contains less than about 0.05% of higher fatty acids). In another embodiment, the first composition is free of higher fatty acids (i.e., contains less than about 0.025% of higher fatty acids). In yet another embodiment, the first composition contains no higher fatty acids.

Second Composition

According to the present invention, a second composition comprising at least one oxidizing agent is provided. By "oxidizing agent," it is meant that the agent causes another compound to be oxidized (that is, gain oxygen). Oxidizing agents can be of varying strength. For example, oxidizing agents can be strong or weak. Strong oxidizing agents have an oxidation potential (v) greater than 1.5. Weak oxidizing agents have an oxidation potential (v) less than 1.5.

Acceptable oxidizing agents include, but are not limited to, peroxides such as hydrogen peroxide, calcium peroxide, magnesium peroxide, melamine peroxide, sodium carbonate peroxide, strontium peroxide, urea peroxide and zinc peroxide, persulfates such as ammonium persulfate and sodium persulfate, and halogenates, halogenides and halogenites such as potassium bromate, potassium chlorate, sodium bromate, sodium chlorate, sodium chlorite, sodium iodate and ferric chloride. Preferred oxidizing agents are peroxides. A particularly preferred oxidizing agent is hydrogen peroxide.

Preferably, the oxidizing agent is present in an amount ranging from about 1% to about 90% by weight of the total weight of the second composition, more preferably from about 5% to about 70% of the total weight of the second composition, more preferably from about 10% to about 50% of the total weight of the second composition, and most preferably from about 20% to about 40% of the total weight of the second composition, including all ranges and subranges therebetween.

Additional Ingredients

The first and second compositions of the present invention can also comprise any additive usually used in the field under consideration. For example, dispersants, antioxidants, essential oils, preserving agents, surfactants, fragrances, liposoluble polymers that are dispersible in the medium, fillers, neutralizing agents, cosmetic and dermatological active agents, emollients, moisturizers, surfactants, vitamins, essential fatty acids, sunscreens, film forming agents, colorants, and mixtures thereof can be added. A non-exhaustive listing of such ingredients can be found in U.S. patent application publication no. 2004/0170586, the entire contents of which is hereby incorporated by reference. Further examples of suitable additional components can be found in the other references which have been incorporated by reference in this application, including but not limited to the applications from which this application claims priority. Still further examples of such additional ingredients may be found in the *International Cosmetic Ingredient Dictionary and Handbook* (9th ed. 2002).

A person skilled in the art will take care to select the optional additional additives and/or the amount thereof such that the advantageous properties of the compositions according to the invention are not, or are not substantially, adversely affected by the envisaged addition.

These substances may be selected variously by the person skilled in the art in order to prepare a composition which has the desired properties, for example, consistency or texture.

These additives may be present in the compositions in a proportion from 0% to 99% (such as from 0.01% to 90%) relative to the total weight of the composition and further such as from 0.1% to 50% (if present).

In particular, with respect to compositions for application to hair, additional optional ingredients include but are not limited to those ingredients set forth in U.S. Pat. No. 6,548,051 and U.S. patent application publication nos. 2002/0059941 and 2006/0024255, the entire contents of which are herein incorporated by reference. Examples of such additional ingredients include but are not limited to anionic surfactants, adhesive particles, non-adhesive particles, fixing polymers, and propellants (for aerosol compositions).

Specific examples of additional ingredients include oils, particularly if the composition is an anhydrous composition or an emulsion. Any oils can be used in accordance with the present invention. Preferably, the oils, if present, represent from about 5% to about 80% by weight of the total weight of the composition, more preferably from about 10% to about 60% of the total weight of the composition, and most preferably from about 15% to about 50%, including all ranges and subranges therebetween.

Examples of acceptable surfactants include anionic, nonionic, amphoteric, zwitterionic and cationic surfactants. Specific examples of acceptable surfactants can be found, for example, in U.S. Pat. Nos. 6,153,208, 6,338,842, and 6,432,894, and U.S. patent application publication no. 2002/0013972, the entire contents of which are hereby incorporated by reference.

Water, when present, preferably represents from about 1% to about 70% by weight of the total weight of the composition, more preferably from about 5% to about 60% of the total weight of the composition, and most preferably from about 10% to about 50%, including all ranges and subranges therebetween.

According to the present invention, methods for removing artificial color from hair comprising combining a first composition comprising a sulfur reducing agent with a second composition comprising an oxidizing agent to form a color removing composition; and using the color removing composition to remove artificial color from the hair are provided. Preferably, combining the first and second compositions occurs at room temperature (approximately 25° C.), or at a slightly elevated temperature (approximately 30° C.-45° C.).

Also preferably, when the first and second compositions are combined to form a color removing composition, the color removing composition has an acidic pH. Most preferably, the pH of the color removing composition is between 0 and 5, with a pH of between 2 and 4 being most preferred given that the color removing composition thus prepared will be applied to the hair of living subjects.

Also preferably, when the first and second compositions are combined to form a color removing composition, the color removing composition is a non-viscous composition having a viscosity of less than 650 cps, preferably less than 600 cps, and more preferably less than 500 cps.

In accordance with the present invention, when the first and second compositions are combined to form a color removing composition, an exothermic reaction temperature occurs. Such exothermic reaction conditions permit effective removal of artificial color from hair. Preferably, this exothermic reaction temperature is at least about 30° C., preferably is at least about 35° C., preferably is at least about 40° C., and most preferably is at least about 45° C. Given that the color removing composition thus prepared will be applied to the hair of living subjects, the preferred range for exothermic reaction temperature is from 35° C. to 45° C. To achieve such preferred exothermic reaction temperatures, the sulfur reducing agent should be employed in molar excess relative to the oxidizing agent in the color removing composition. The precise molar excess amount will depend on the specific sulfur reducing and oxidizing agents used and, once chosen, can be determined by those skilled in the art.

According to preferred embodiments of the present invention, the first composition and the second composition are combined to form a color removing composition prior to application of either composition to the hair, and the color removing composition is subsequently applied to the hair. The color-removing composition thus formed comprises the ingredients of both the first composition and the second composition, meaning that the preferred ranges for such ingredients in the color-removing composition are about half of the ranges set forth above for the individual compositions (for example, the most preferred range for both the sulfur reducing agent and the oxidizing agent in the color-removing composition is from about 10% to about 20% by weight with respect to the total weight of the composition).

According to other preferred embodiments, the first composition and the second composition are combined on the hair to form a color removing composition: that is, one composition is applied to the hair, and then the other composition is sequentially (or simultaneously) applied to the hair. After both compositions have been applied to the hair, the compositions can be combined to form a color removing composition.

According to the methods of the present invention, once the color removing composition has been formed, the color removing composition is used to remove artificial color from hair. By "removing artificial color" from hair, it is meant that at least some of the artificial color on the hair is removed from the hair. According to some preferred embodiments of the present invention, the amount of artificial color removed from hair is substantially all hair color: that is, the amount of artificial hair color removed is sufficient to restore hair to its natural color.

According to one preferred embodiment of the present invention, methods for removing artificial color from artificially colored hair comprising combining a first composition comprising a sulfur reducing agent with a second composition comprising an oxidizing agent to form a color removing composition; and using the color removing composition to remove color from the artificially colored hair are provided. As indicated above, according to particularly preferred embodiments, all or substantially all artificial hair color is removed from the artificially colored hair.

According to another preferred embodiment of the present invention, methods for highlighting artificially colored hair comprising combining a first composition comprising a sulfur reducing agent with a second composition comprising an oxidizing agent to form a color removing composition; and using the color removing composition to highlight artificially colored hair are provided.

While not wishing to be bound by any particular theory, it is believed that combining a first composition comprising a sulfur reducing agent and a second composition comprising an oxidizing agent creates a controllable exothermic redox reaction. The heat provided by the exothermic reaction allows the interactions between or among the artificial color and the hair to be sufficiently interfered with to allow the artificial color to be removed from hair safely and effectively.

Thus, in accordance with preferred embodiments of the present invention, the first and second compositions are combined to form a color removing composition shortly before use of the color removing composition. For example, the first and second compositions can be combined immediately prior to use, 10 seconds prior to use, 20 seconds prior to use, etc. However, it is to be understood that the longer period of time which elapses between combining the first and second compositions to form a color removing composition and using the color removing composition to remove hair color, the less exothermic energy should be available to remove hair color. Accordingly, combining the first and second compositions to form a color removing composition immediately prior to use of the color removing composition is preferred.

According to preferred embodiments, the methods for removing artificiall hair color of the present invention can be performed one or more times per sitting or one or more times per day. For example, the first and second compositions can be combined to form a color removing composition, and the color removing composition can be used to remove artificial hair color. If further artificial hair color removal is desired, this process can be repeated until the desired amount of artificial hair color removal has been achieved.

Also according to preferred embodiments, the color removing composition is applied to hair for an amount of time sufficient to remove artificial hair color. Generally speaking, the color removing composition can be applied to hair for at least 5 minutes, preferably for at 30 minutes.

The present invention also envisages kits and/or prepackaged materials suitable for consumer use containing one or more compositions according to the description herein. According to preferred embodiments, a kit comprising: (a) a first composition comprising a sulfur reducing agent; (b) a second composition comprising an oxidizing agent; and (c) instructions for combining the first composition and the second composition to form a color removing composition and for using the color removing composition to remove artificial color from the hair is provided. The instructions for such a kit could be contained anywhere in the kit such as, for example, on the packaging or on a separate insert within the kit. Such kits may also include other compositions such as, for example, a hair coloring or hair dyeing composition.

The packaging and application device for any subject of the invention may be chosen and manufactured by persons skilled in the art on the basis of their general knowledge, and adapted according to the nature of the composition to be packaged. Indeed, the type of device to be used can be in particular linked to the consistency of the composition, in particular to its viscosity; it can also depend on the nature of the constituents present in the composition, such as the presence of volatile compounds.

Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention.

Notwithstanding that the numerical ranges and parameters setting forth the broad scope of the invention are approximations, the numerical values set forth in the specific examples are reported as precisely as possible. Any numerical value, however, inherently contain certain errors necessarily resulting from the standard deviation found in their respective measurements. The following examples are intended to illustrate the invention without limiting the scope as a result. The percentages are given on a weight basis.

EXAMPLE A

First Composition

| INCI Name | Percent |
|---|---|
| Deionized Water | 47.82 |
| Ammonium Thioglycolate | 6.75 |
| Thiolactic Acid | 3.75 |
| Ammonium Bisulfite | 11.25 |
| Sodium Bisulfite | 12.75 |
| Monoethanolamine | 4.00 |
| Sodium Polystyrene Sulfonate | 3.68 |
| Sodium C14-16 Olefin Sulfonate | 10.00 |
| Total | 100.00 |

EXAMPLE B

First Composition

| INCI Name | Percent | Activity | Amount |
|---|---|---|---|
| Deionized Water | 45.82 | | 228.96 |
| Ammonium Thioglycolate | 6.75 | 59.76% | 33.89 |
| Thiolactic Acid | 3.75 | | 18.75 |
| Ammonium Bisulfite | 11.25 | 70.28% | 56.25 |
| Sodium Bisulfite | 12.75 | 40.00% | 63.75 |
| Monoethanolamine | 4.00 | | 20.00 |
| Sodium Polystyrene Sulfonate | 3.68 | | 18.40 |
| Sodium C14-16 Olefin Sulfonate | 10.00 | | 50.00 |
| Ascorbic Acid | 2.00 | | 10.00 |
| Total | 100.00 | | 500.00 |

EXAMPLE C

First Composition

| INCI Name | Percent |
|---|---|
| Deionized Water | Qs |
| Ammonium Thioglycolate | 4-15 |
| Thiolactic Acid | 4-15 |
| Ammonium Bisulfite | 4-14 |
| Sodium Bisulfite | 4-14 |
| Monoethanolamine | 2-6 |
| Surfactants | 7-20 |
| Total | 100 |

EXAMPLE D

Second Composition

| INCI Name | Percent |
|---|---|
| Deionized Water | 91.32 |
| Pentasodium Pentetate | 0.15 |
| Trideceth-2 Carboxamide MEA | 0.85 |
| Cetearyl Alcohol (and) Ceteareth-25 | 2.85 |
| Glycerin | 0.50 |
| Sodium Stannate | 0.04 |

EXAMPLE D-continued

Second Composition

| INCI Name | Percent |
|---|---|
| Tetrasodium Pyrophosphate | 0.02 |
| Hydrogen Peroxide | 4.00 |
| Phosphoric Acid | 0.27 |
| Total | 100% |

What is claimed is:

1. A method for removing artificial color from hair, comprising:
   combining a first composition comprising a sulfur reducing agent with a second composition comprising an oxidizing agent prior to application of either composition to the hair, to form an artificial color removing composition;
   applying the artificial color removing composition to artificially colored hair; and
   removing the artificial color from the hair;
   wherein
   at least one of the first composition and the second composition comprise at least one surfactant, and
   a molar amount of the sulfur reducing agent in the color removing composition is in a molar excess relative to the molar amount of the oxidizing agent.

2. The method of claim 1, wherein the sulfur reducing agent in the first composition is selected from the group consisting of sulfur hydroxy acids, salts of sulfur hydroxy acids, salts of sulfites or bisulfites, sulfur antioxidants, and mixtures thereof.

3. The method of claim 2, wherein the sulfur reducing agent is a sulfur hydroxyl acid or salt of a sulfur hydroxyl acid selected from the group consisting of thioglycolic acid, thiolactic acid, salts of thioglycolic acid, salts of thiolactic acid, and mixtures thereof.

4. The method of claim 2, wherein the sulfur reducing agent is a salt of a bisulfite selected from the group consisting of sodium bisulfite, potassium bisulfite, calcium bisulfite, magnesium bisulfite, ammonium bisulfite, and mixtures thereof.

5. The method of claim 1, wherein the oxidizing agent in the second composition comprises a strong oxidizing agent.

6. The method of claim 1, wherein the oxidizing agent in the second composition comprises hydrogen peroxide.

7. The method of claim 2, wherein the oxidizing agent in the second composition comprises hydrogen peroxide.

8. The method of claim 3, wherein the oxidizing agent in the second composition comprises hydrogen peroxide.

9. The method of claim 4, wherein the oxidizing agent in the second composition comprises hydrogen peroxide.

10. The method of claim 1, wherein a pH of the color removing composition is between 1 and 5.

11. The method of claim 10, wherein the pH of the color removing composition is between 2 and 4.

12. The method of claim 1, wherein a viscosity of the color removing composition is less than 600 cps.

13. The method of claim 1, wherein the first composition is substantially free of higher fatty acids.

14. The method of claim 1, wherein the first composition contains no higher fatty acids.

15. The method of claim 1, wherein a content of the sulfur reducing agent in the first composition is 5 to 70 percent by weight of the weight of the first composition.

16. The method of claim 1, wherein a content of the oxidizing agent in the second composition is 5 to 70 percent by weight of the weight of the second composition.

17. The method of claim 15, wherein a content of the oxidizing agent in the second composition is 5 to 70 percent by weight of the weight of the second composition.

18. The method of claim 1, wherein the color removing composition is applied to the hair within 20 seconds after the two compositions are combined.

19. The method of claim 1, wherein the first composition further comprises at least one surfactant.

20. The method of claim 1, wherein the second composition further comprises at least one surfactant.

21. The method of claim 1, wherein both the first composition and the second composition comprise at least one surfactant.

* * * * *